US00PP12622P2

(12) United States Plant Patent
Clark et al.

(10) Patent No.: US PP12,622 P2
(45) Date of Patent: May 14, 2002

(54) NECTARINE TREE — NAMED 'WESTBROOK' CULTIVAR

(75) Inventors: John Reuben Clark; James Norman Moore, both of Fayetteville, AR (US)

(73) Assignee: University of Arkansas, Fayetteville, AR (US)

( * ) Notice: Subject to any disclaimer, the term of this patent is extended or adjusted under 35 U.S.C. 154(b) by 7 days.

(21) Appl. No.: 09/689,127

(22) Filed: Oct. 13, 2000

(51) Int. Cl.[7] ..... A01H 5/00
(52) U.S. Cl. ..... Plt./190

(58) Field of Search ..... Plt./190

*Primary Examiner*—Bruce R. Campell
*Assistant Examiner*—Annette H. Para

(57) ABSTRACT

Description and specifications of a new and distinct nectarine variety which orignated from seed produced by a hand pollinated cross of Arkansas Nectarine Selection 172 (non-patented) and Arkansas Nectarine Selection 176 (non-patented) is provided. This new nectarine variety can be distinguished by its very early fruit ripening, attractive, flavorful firm fruits, good plant vigor and productivity, and its high level of genetic resistance to the disease bacterial spot.

3 Drawing Sheets

SUMMARY OF THE INVENTION

The new and distinct variety of nectarine originated from a hand pollinated cross of Arkansas Nectarine Selection 172 (non-patented)×Arkansas Nectarine Selection 176 (non-patented) made in 1977 at the Arkansas Agricultural Experiment Station Fruit Substation at Clarksville, Ark. The parent plants used in this hybridization have not been named and released and are unavailable in commerce.

Plants and fruit of this new variety differ phenotypically from its parents. The new variety is earlier ripening and possesses larger fruit size, better flavor, and more attractive fruit than the parent Arkansas Selection 172, and is earlier ripening, more productive, and has better flavor, more colorful fruit and greater disease resistance than the parent Arkansas Selection 176. Both the parents and the instant variety are the genus and species *Prunus persica*. The new variety ripens its fruit very early, before either of the parent nectarines and before most extant nectarine cultivars.

The seeds resulting from this controlled hybridization were germinated in a greenhouse in the spring of 1978 and planted in a field on the Arkansas Agricultural Experiment Station in Clarksville, Ark. The seedlings fruited during the summer of 1980 and one, designated Arkansas 236, was selected for its very early ripening, attractive fruit shape and color, good fruit quality, and resistance to bacterial spot. During 1980, the original plant selection was propagated asexually, at the above noted location, by budding onto standard peach rootstock variety 'Lovell' (non-patented) and a test plot of two plants was established. Subsequently, larger test plantings have been established with asexually multiplied plants at two additional locations in Arkansas (Clarksville and Hope, Ark.).

The new variety has been asexually multiplied several times since 1980 at this location by budding onto 'Lovel' peach rootstock and no incompatibility with peach rootstocks has occurred following budding. During all asexual multiplication, the characteristics of the original plant have been maintained and no aberrant phenotypes have appeared.

Plants of the new variety are vigorous and productive, and trees are standard in size, well branched and symmetrical with an upright growth habit, comparable to other nectarine or peach trees (*Prunus persica*). Trees express a high level of resistance to both foliar and fruit infection of bacterial spot [*Xanthomonas campestris* pv. pruni (Smith) Dye]. The new variety consistently is more resistant to bacterial spot than are the standard nectarine varieties 'Redgold' (U.S. Plant Pat. No. 1,329) and 'Summer Beaut' (U.S. Plant Pat. No. 4,309). The new variety blooms in the spring with 'Summer Beaut' and 1 to 2 days later than 'Redgold'. No winter cold injury has been observed on wood or buds of the new variety in Arkansas tests where minimum temperatures have reached −23° C. Chilling requirement to break dormancy is estimated to be 750 hours below 7° C.

Fruit of the new variety ripens very early, averaging 4 weeks earlier than 'Summer Beaut', 6 weeks before 'Redgold', and 3 weeks before the reference peach variety, 'Redhaven' (non-patented). Average ripening date is June 9 in west-central Arkansas. Despite the very early ripening, fruit of the new variety rarely has split pits, a serious fruit disorder common in most early ripening peaches and nectarines. Fruit yields have been good and have averaged equal to or higher than the comparison nectarine varieties 'Redgold' and 'Summer Beaut' in all test comparisons.

The fruit is round in shape, without a prominent tip or bulging suture. Fruits are attractive with 80% bright red, 20% yellow skin color. Fruit finish is good with no blemishes. The fruit skin is tender and occasionally cracks on fully ripe fruit following rainfall. The flesh of the fruit is bright yellow in color and has little red pigment in the flesh. Flesh is melting in texture but is firm and retains firmness well after maturity. Fruit is medium, averaging 109.6 g, and careful management of crop load is required to produce good fruit size.

The fresh fruit rates good in flavor, and is exceptionable favorful for a very early ripening nectarine. Fruits average 10.7% soluble solids and receive high scores in taste panels for flavor. The flavor is sweet and mildly subacid, with a distinct nectarine aroma.

The distinctive features of the new variety are its very early ripening, attractive flavorful firm fruits, good plant vigor and productivity, and its high level of resistance to bacterial spot.

The new variety has been named the 'WESTBROOK' cultivar.

BRIEF DESCRIPTION OF THE PHOTOGRAPHS

The accompanying photographs show typical specimens of the fruit (FIGS. 1 and 2) and leaf (FIG. 3) of the new variety in color as nearly true as it is reasonably possible to make in a color illustration of this character.

DETAILED DESCRIPTION OF THE NEW VARIETY

The following is a detailed description of the botanical and pomological characteristics of the subject nectarine. Color data are presented in Royal Horticultural Society Colour Chart designations and are supplemented with readings from a Minolta Chroma Meter CR-200, version 3.0, which measures absolute chromaticity in tristimulus values L, a, and b. Calibration was performed using a standard white plate supplied by the manufacturer.

Where dimensions, sizes, colors and other characteristics are given, it is to be understood that such sharacteristics are approximations of averages set forth as accurately as practical.

The descriptions reported herein are from specimens grown in Clarksville, Ark. and are from trees grown in trickle (drip) irrigated orchards growing on a Linker fine sandy loam soil. The data were collected from eight-year old trees of the instant variety except yield data that were taken on five-year-old trees in a replicated test planting.

Plant:

*Size.*—Mature trees (5 years of age and older) average 3.4 m to 3.7 m in height and 4.7 to 5.6 m in spread or width, and upright growth habit, as grown on 'Lovell' rootstock using an open-center training system commonly used on nectarines. Tree size is comparable to that of the 'Red Gold' and 'Summer Beaut' varieties.

*Growth.*—Vigorous, symmetrical form, good canopy development. Vigor comparable to that of the 'Red Gold' and 'Summer Beaut' varieties.

*Productivity.*—Very productive and consistent from year to year. Yield measured 26.3 kg/tree on five-year old trees and just under that of 'Summer Beaut' with 30.8 kg/tree but exceeding that of 'Red Gold' of 16.7 kg/tree in a test planting of identical age and growing conditions.

*Cold hardiness.*—Wood and dormant buds hardy to −23° C.

*Disease resistance.*—Leaves and fruit resistant to bacterial spot under growing conditions where bacterial spot infection is often very severe on susceptible genotypes. No bactericides were used in the development or evaluation of the instant cultivar. Evidence of bacterial spot infection less than that of 'Red Gold' and 'Summer Beaut' varieties in all years of evaluation. A commercial fungicide program was utilized in orchards used in the development and evaluation of the instant variety, thus no resistance to brown rot or scab, the other common diseases at Clarksville, Ark., was determined.

*Insect resistance.*—Insecticides were applied to orchards used in the development of the instant variety to control the common insects at the location including oriental fruit moth, plum curulio, stinkbug, tarnished plant bug, lesser peach tree borer and greater peach tree borer. Therefore no insect resistance was determined in the testing of the instant variety.

Foliage:

*Shoots.*—Glabrous. Mature shoot length 83.4 cm; diameter base 7.8 mm, midpoint 5.1 mm, terminal 2.5 mm. Mature shoot color adaxial side: Greyed Orange Group (176A), L=41.64, a=21.91, b=12.86; Mature shoot color abaxial side: Yellow Green Group (145A).

*Leaves.*—Simple, alternate, glabrous, lanceolate, petiolate, deciduous. Venation pinnate; base acute; terminal or apex acuminate; margin serrated. mature leaf size: length 15.3 cm; diameter midpoint 3.98 cm. Leaf serrations; 4.25/cm. Mature leaf color: Abaxial-Yellow Green Group (147B), L=45.41, a=−11.33, b=18.50 and anthocyanin present on the abaxial midrib only (central vein) on mature leaves; Young leaf color: abaxial-Green Group (138B), L=48.37, a=−15.80, b=24.87 ; adaxial-Yellow Green Group (146B), L=44.23, a=−17.50, b=25.17 and anthocyanin not present on abaxial or adaxial side of young leaves on midrib or other location. Pedicel length—mature leaf: 9.4 mm and anthocyanin present on adaxial and abaxial sides of mature leaf petiole and absent on young leaf petiole. Leaf glands: reniform, 3 per leaf, located on basal portion of leaf blade near juncture with petiole. Leaf glands are 0.76 mm in width and 1.15 mm in length and color of glands is Brown Group (200C). Leaf scar beneath bud at the end of the growing season 4 mm wide.

*Buds.*—Flower buds ovoid in shape; size at the termination of the growing season 4 mm long and 3 mm wide; dormant flower bud color Greyed Orange Group (177 A). Number of leaf buds per 15 cm: 7. Number of flower buds per 15 cm: 10. Mature shoot internode length: base 12 mm, midpoint 6 mm, terminal 10 mm.

Bark (of mature trunk of tree):

*Color.*—Grey Group (201D); L=54.85, a=4.08, b=7.62.

Flowers: Bloom occurs prior to vegetative bud break; solitary to occasional double individual flowers at a single node; perfect; self-fertile.

*Date of bloom.*—First, Julian 71 (March 11); Full, Julian 88 (March 28).

*Size.*—Diameter fully open 23.8 mm.

*Type.*—Non-showy.

*Color.*—Red Purple Group (62A), L=71.43, a=42,82, b=0.44.

*Petals per flower.*—5.

*Length of pistil.*—1.64 cm.

*Stamens*—Numerous with pollen present, fertile and abundant.

Fruit:

*Size.*—Medium, avg. 109.6 g; diameter stem end 5.82 cm, equator 6.30 cm, blossom end 5.56 cm; length base to apex 5.88 cm.

*Shape.*—Round, symmetrical, without pronounced tip or suture bulge.

*Skin.*—Glabrous, attractive; ground color Orange Red Group (34A, L=56.70, a=29.24, b=37.83, with red blush (Red Group 53A), L=32.56, a=28.70, b=8.59 over 80% of surface. Skin thin and tenacious to flesh; tendency to crack following rain.

*Flesh.*—Uniform Yellow Orange (20A), L=58.31, a=11.41, b=42.23; semi-clingstone; melting texture; good firmness. Firmness when measured by a fruit pressure tester (using a McCormick model FT327 fruit pressure tester, 11 mm diameter probe, McCormick Fruit Tree Co., Yakima, Wash.) had average firmness value of 4.6 kg. Good eating quality; flavor sweet, subacid, with mild nectarine aroma.

*Pedicel length.*—8.3 mm.

*Ripe date.*—June 9 (Julian 161) in west-central Arkansas. Ripening of individual fruit is uniform.

*Tendency of pit to split.*—Variable among years with no split pits most years up to a a maximum of 20% split pits measured.

*Soluble solids.*—10.7%

Pit/stone:

*Size.*—Length 3.62 cm; diameter (midpoint) 2.32 cm.

*Shape.*—Slightly oblong with deep furrowing and pitting.

*Color.*—Greyed Orange Group (164B), L=55.21, a=12.23, b=32.08.

Kernel:

*Size.*—Length 14.8 mm; width 9.3 mm; diameter varies with dryness of the kernel but is up to 2 mm.

*Shape.*—Elliptical with a straight or slightly curved apiculate apex.

*Color.*—Greyed Orange Group (165B).

Uses: Fresh consumption, canned, frozen; not evaluated for drying or other uses.

The variety: The most distinctive features of the variety are its very early ripening, attractive flavorful firm fruits, good plant vigor and productivity, and its high level of resistance to the disease bacterial spot.

We claim:

1. A new and distinct variety of nectarine, substantially as illustrated and described, characterized by its very early ripening, attractive flavorful firm fruits, good plant vigor and productivity, and its high level of resistance to the disease bacterial spot.

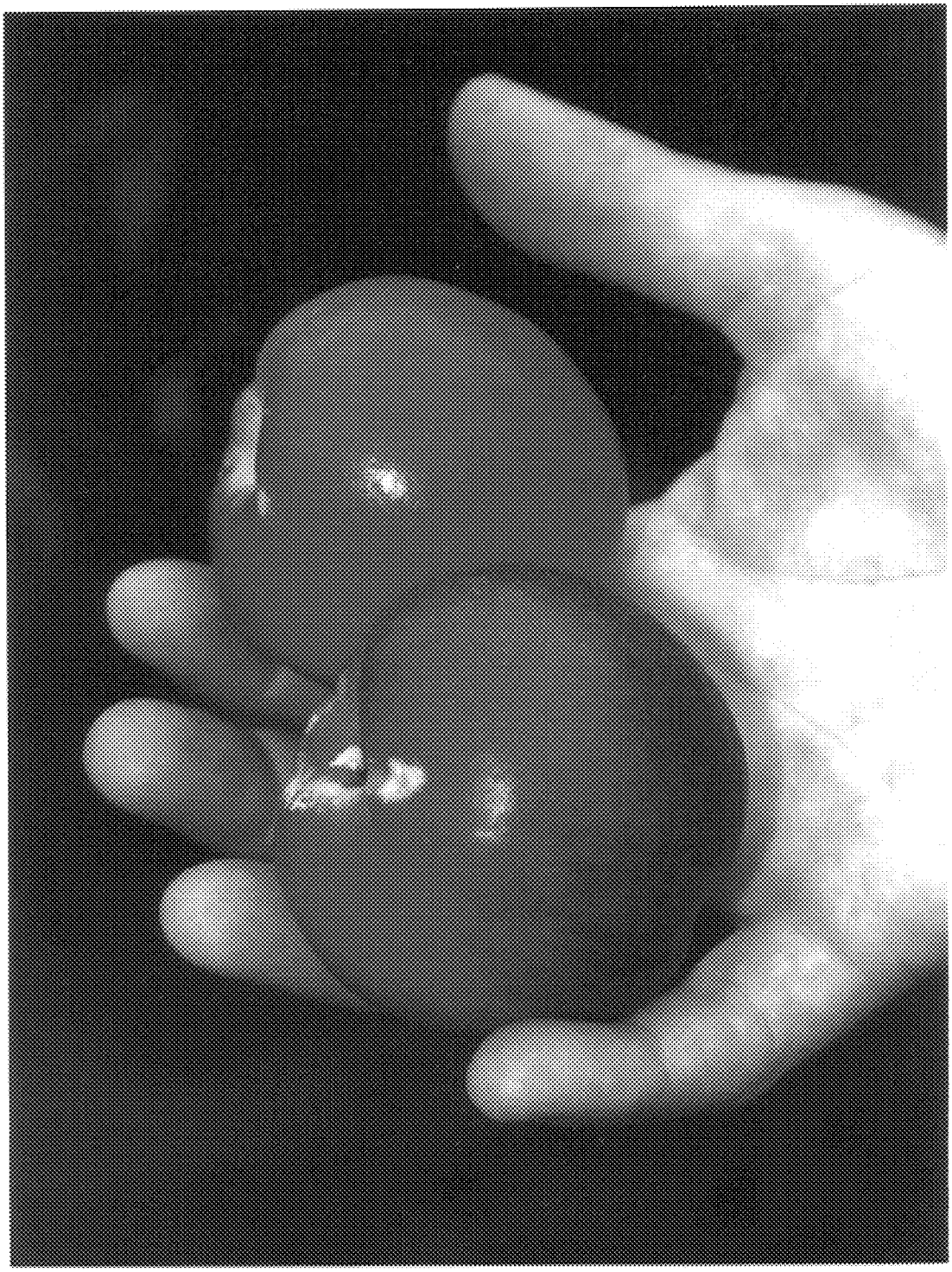

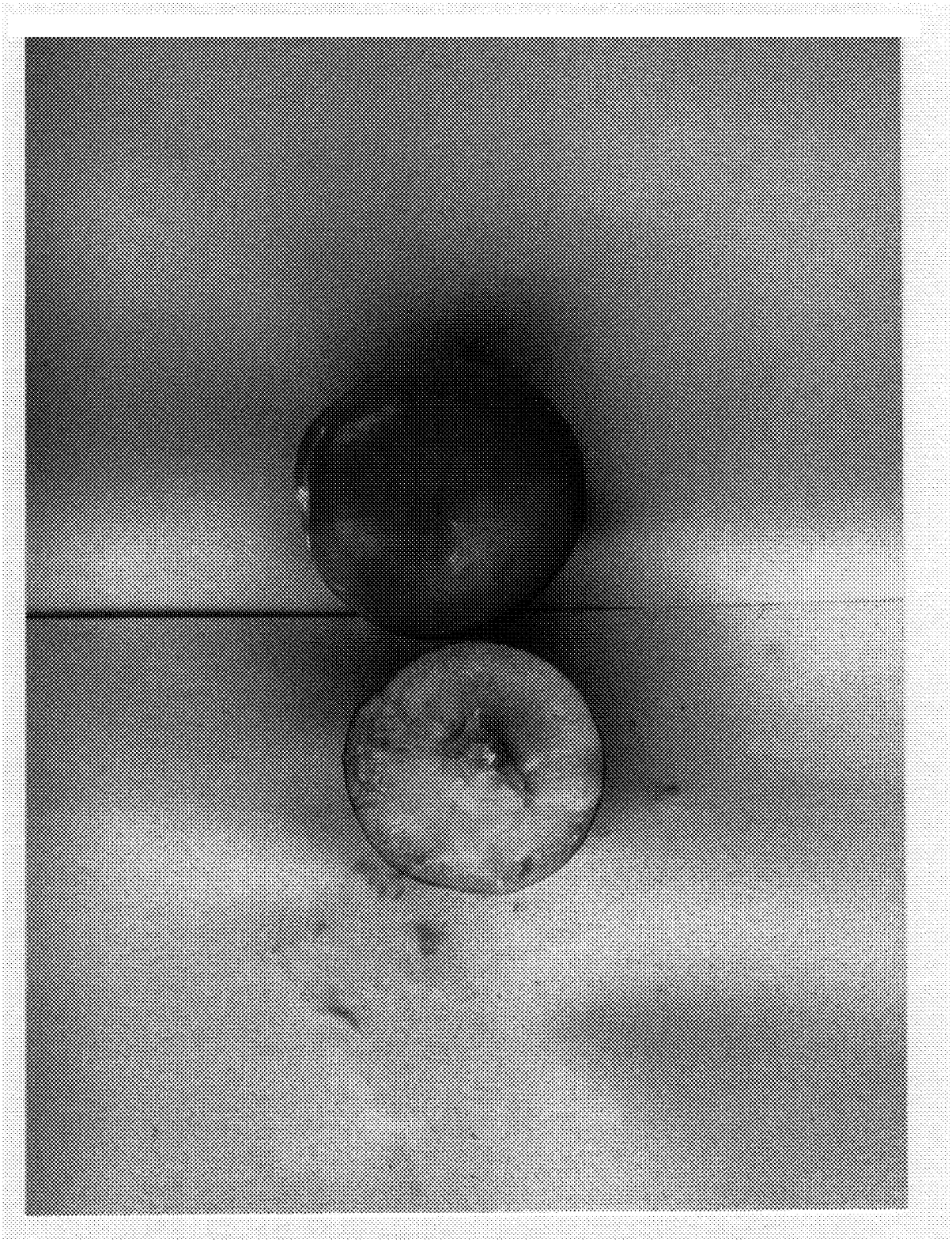

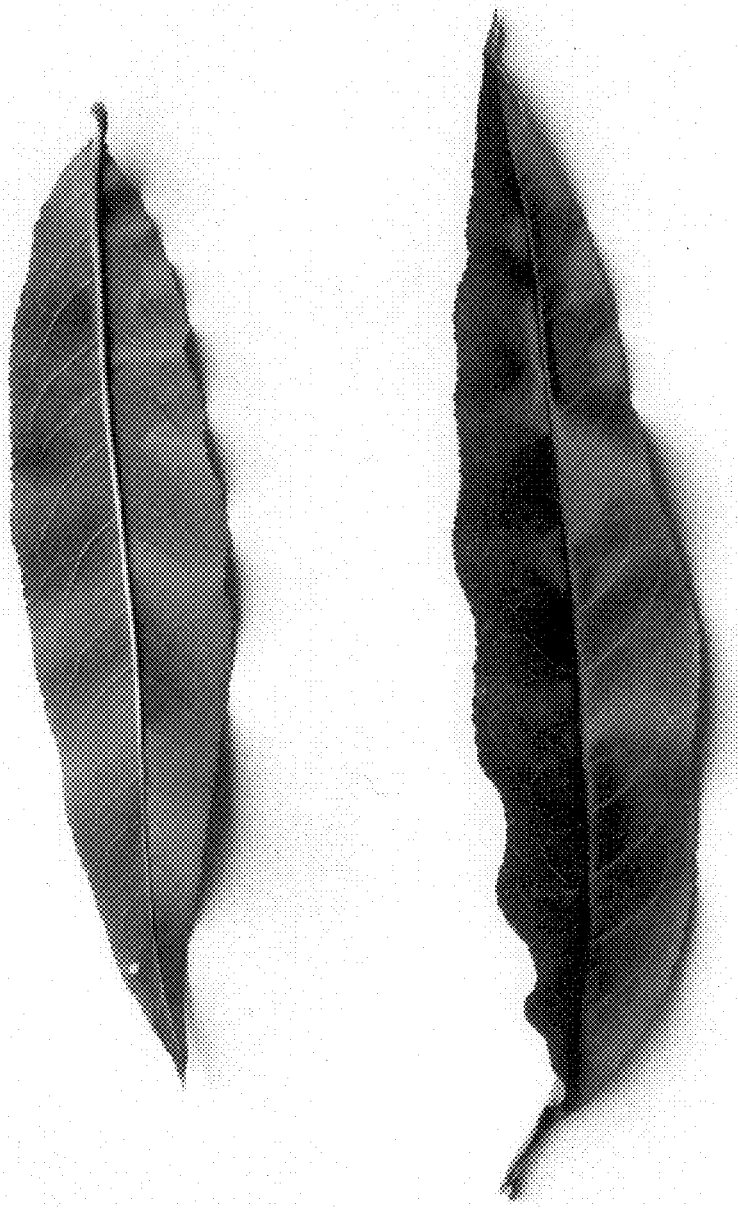

* * * * *